United States Patent [19]

Alikhan

[11] Patent Number: 5,580,418
[45] Date of Patent: Dec. 3, 1996

[54] APPARATUS FOR MAKING FILM LAMINATED MATERIAL

[75] Inventor: Mir I. Alikhan, Marietta, Ga.

[73] Assignee: Kimberly-Clark Corporation, Neenah, Wis.

[21] Appl. No.: 349,145

[22] Filed: Dec. 2, 1994

Related U.S. Application Data

[63] Continuation of Ser. No. 973,145, Nov. 6, 1992, Pat. No. 5,370,764.

[51] Int. Cl.⁶ ..................................................... B32B 31/04
[52] U.S. Cl. .......................... 156/553; 156/209; 156/252; 156/269; 156/290; 156/324; 156/459; 156/543; 156/555
[58] Field of Search ..................................... 156/209, 252, 156/253, 553, 290, 555, 554, 581, 154

[56] References Cited

U.S. PATENT DOCUMENTS

| | | |
|---|---|---|
| D. 239,137 | 3/1976 | Appleman . |
| D. 259,219 | 5/1981 | Bates . |
| D. 311,997 | 11/1990 | Legare . |
| D. 313,319 | 1/1991 | Legare . |
| D. 313,512 | 1/1991 | Legare . |
| D. 314,672 | 2/1991 | Legare . |
| D. 314,673 | 2/1991 | Legare . |
| 3,024,154 | 3/1962 | Singleton et al. . |
| 3,292,619 | 12/1966 | Egler . |
| 3,307,961 | 3/1967 | Stiehl et al. . |
| 3,441,021 | 4/1969 | Endres . |
| 3,459,618 | 8/1969 | Egler . |
| 3,507,943 | 4/1970 | Such et al. ............................ 264/103 |
| 3,508,991 | 4/1970 | Yunan . |
| 3,542,634 | 11/1970 | Such et al. ............................... 161/38 |
| 3,604,062 | 9/1971 | Hollingsworth . |
| 3,604,475 | 9/1971 | Hollingsworth . |
| 3,676,242 | 7/1972 | Prentice . |

(List continued on next page.)

FOREIGN PATENT DOCUMENTS

| | | |
|---|---|---|
| 1086627 | 9/1980 | Canada . |
| 2009807 | 8/1991 | Canada . |
| 1288584 | 9/1991 | Canada . |
| 0006264 | 1/1980 | European Pat. Off. . |
| 0010439 | 4/1980 | European Pat. Off. . |
| 0019754 | 12/1980 | European Pat. Off. . |
| 0040447 | 1/1981 | European Pat. Off. . |
| 0039973 | 11/1981 | European Pat. Off. . |
| 0039974 | 11/1981 | European Pat. Off. . |
| 0040084 | 11/1981 | European Pat. Off. . |
| 0006647 | 7/1983 | European Pat. Off. . |
| 0158490 | 10/1985 | European Pat. Off. . |
| 0160569 | 11/1985 | European Pat. Off. . |
| 0172420 | 2/1986 | European Pat. Off. . |
| 0176914 | 4/1986 | European Pat. Off. . |
| 0053928 | 5/1986 | European Pat. Off. . |
| 0203823 | 12/1986 | European Pat. Off. . |
| 0205286 | 12/1986 | European Pat. Off. . |
| 0214608 | 3/1987 | European Pat. Off. . |
| 0217032 | 4/1987 | European Pat. Off. . |
| 0219978 | 4/1987 | European Pat. Off. . |
| 0252041 | 1/1988 | European Pat. Off. . |
| 0260131 | 3/1988 | European Pat. Off. . |
| 0262817 | 4/1988 | European Pat. Off. . |
| 0286409 | 10/1988 | European Pat. Off. . |
| 0140560 | 11/1988 | European Pat. Off. . |

(List continued on next page.)

*Primary Examiner*—Jeff H. Aftergut
*Attorney, Agent, or Firm*—Nicholas N. Leach

[57] ABSTRACT

This invention relates to a film laminated material wherein a first film layer comprising a thin film of a thermoplastic material and a second fibrous layer comprising a plurality of staple fibers or continuous filaments of two or more thermoplastic or other materials are bonded together in a spaced apart bonding pattern having apertures formed therein to form a film laminate having improved liquid distribution and management properties as well as enhanced comfort and softness when placed in contact with human skin. Also disclosed are a method and apparatus for making such a film laminate.

11 Claims, 7 Drawing Sheets

U.S. PATENT DOCUMENTS 3,765,974 10/1973 Petersik et al. .
3,811,979 5/1974 Dempsey et al. .
3,888,254 6/1975 Hendricks .
3,945,386 3/1976 Anczurowski .
3,949,127 4/1976 Ostermeier .
3,953,638 4/1976 Kemp .
3,965,906 6/1976 Karami .
3,967,623 7/1976 Butterworth .
3,994,299 11/1976 Karami .
4,014,341 3/1977 Karami .
4,035,219 7/1977 Cumbers .
4,039,711 8/1977 Newman .
4,041,203 8/1977 Brock et al. .
4,073,991 2/1978 Focht .
4,088,726 5/1978 Cumbers .
4,128,679 12/1978 Pohland .
4,209,563 6/1980 Sisson .
4,216,772 8/1980 Tsuchiya et al. .
4,285,342 8/1981 Mesek .
4,296,168 10/1981 Ambrose .
4,323,069 4/1982 Ahr et al. .
4,324,246 4/1982 Mullane et al. .
4,333,465 6/1982 Wiegner .
4,333,979 6/1982 Sciaraffa et al. .
4,340,563 7/1982 Appel et al. .
4,377,615 3/1983 Suzuki et al. .
4,379,198 4/1983 Jaeschke et al. .
4,392,862 7/1983 Marsan et al. .
4,397,644 8/1983 Matthews et al. .
4,417,893 11/1983 Mizutani et al. .
4,451,520 5/1984 Tecl et al. .
4,469,734 9/1984 Minto et al. .
4,480,000 10/1984 Watanabe et al. .
4,488,928 12/1984 Ali Khan et al. .
4,518,451 5/1985 Luceri et al. .
4,519,799 5/1985 Sakurai et al. .
4,522,203 6/1985 Mays .
4,560,372 12/1985 Pieniak .
4,568,581 2/1986 Peoples, Jr. .
4,578,069 3/1986 Whitehead et al. .
4,588,630 5/1986 Shimalla .
4,592,943 6/1986 Cancian et al. .
4,610,352 9/1986 Howey et al. .
4,626,254 12/1986 Widlund et al. .
4,627,848 12/1986 Lassen et al. .
4,629,457 12/1986 Ness .
4,634,440 1/1987 Widlund et al. .
4,650,481 3/1987 O'Connor et al. .
4,652,484 3/1987 Shiba et al. .
4,667,665 5/1987 Blanco et al. .
4,675,013 6/1987 Ruffo .
4,681,793 7/1987 Linman et al. .
4,690,679 9/1987 Mattingly, III .
4,704,116 12/1987 Enloe .
4,710,186 12/1987 DeRossett et al. .
4,725,473 2/1988 Van Gompel .
4,726,976 2/1988 Karami et al. .
4,737,404 4/1988 Jackson .
4,755,413 7/1988 Morris .
4,761,322 8/1988 Raley .
4,762,520 8/1988 Wallstrom .
4,770,657 9/1988 Ellis et al. .
4,778,460 10/1988 Braun et al. .
4,781,710 11/1988 Megison et al. .
4,781,962 11/1988 Zamarripa et al. .
4,783,231 11/1988 Raley .
4,787,947 11/1988 Mays .
4,794,034 12/1988 Nishizawa et al. .
4,798,603 1/1989 Meyer et al. .
4,798,604 1/1989 Carter .
4,804,378 2/1989 Shiba et al. .
4,806,411 2/1989 Mattingly, III .
4,844,965 7/1989 Foxman .
4,847,134 7/1989 Fahrenkrug .
4,850,990 7/1989 Huntoon et al. .
4,854,984 8/1989 Ball et al. .
4,857,065 8/1989 Seal .
4,878,974 11/1989 Kagawa .
4,886,697 12/1989 Perdelwitz, Jr. .
4,891,258 1/1990 Fahrenkrug .
4,892,535 1/1990 Bjornberg et al. .
4,908,026 3/1990 Sukiennik et al. .
4,929,303 5/1990 Sheth .
4,994,053 2/1991 Lang .
4,995,930 2/1991 Merz et al. .
5,009,651 4/1991 Kamishioiri .
5,030,229 7/1991 Yang .
5,078,710 1/1992 Suda et al. .
5,114,787 5/1992 Chaplin et al. .
5,137,600 8/1992 Barnes et al. .
5,151,091 9/1992 Glaug et al. .
5,171,238 12/1992 Kajander .

FOREIGN PATENT DOCUMENTS 0293482 12/1988 European Pat. Off. .
0294178 12/1988 European Pat. Off. .
0297411 1/1989 European Pat. Off. .
0307116 3/1989 European Pat. Off. .
0309073 3/1989 European Pat. Off. .
0319222 6/1989 European Pat. Off. .
0140470 9/1989 European Pat. Off. .
0336578 10/1989 European Pat. Off. .
0235309 10/1989 European Pat. Off. .
0139484 11/1989 European Pat. Off. .
0173058 3/1990 European Pat. Off. .
0358031 3/1990 European Pat. Off. .
0360929 4/1990 European Pat. Off. .
0370835 5/1990 European Pat. Off. .
0367989 5/1990 European Pat. Off. .
0203821 6/1990 European Pat. Off. .
0207904 6/1990 European Pat. Off. .
0372363 6/1990 European Pat. Off. .
0391661 10/1990 European Pat. Off. .
0395381 10/1990 European Pat. Off. .
0396108 11/1990 European Pat. Off. .
0403187 12/1990 European Pat. Off. .
0423049 4/1991 European Pat. Off. .
0422504 4/1991 European Pat. Off. .
0420256 4/1991 European Pat. Off. .
0421649 4/1991 European Pat. Off. .
0127851 7/1991 European Pat. Off. .
0238334 8/1991 European Pat. Off. .
0245074 9/1991 European Pat. Off. .
0257280 9/1991 European Pat. Off. .
0444671 9/1991 European Pat. Off. .
0242766 3/1992 European Pat. Off. .
0482918 4/1992 European Pat. Off. .
0489205 6/1992 European Pat. Off. .
0492554 7/1992 European Pat. Off. .
0495212 7/1992 European Pat. Off. .
0505027 9/1992 European Pat. Off. .
0523683 1/1993 European Pat. Off. .
0539703 5/1993 European Pat. Off. .
2215178 9/1974 France .
2455884 1/1981 France .
2473304 8/1984 France .
2617682 1/1989 France .
2617683 1/1989 France .
2204855 8/1973 Germany .
2614160 10/1977 Germany .
2925090 1/1980 Germany .
3138852 4/1983 Germany .

| | | |
|---|---|---|
| 3214354 | 10/1983 | Germany . |
| 3245196 | 11/1986 | Germany . |
| 4114839 | 11/1992 | Germany . |
| 47-20257 | 9/1972 | Japan . |
| 61-2854 | 1/1986 | Japan . |
| 1-122727 | 8/1989 | Japan . |
| 8901653 | 1/1990 | Netherlands . |
| 57626 | 11/1985 | Rep. of Korea . |
| 1132120 | 10/1968 | United Kingdom . |
| 1259983 | 1/1972 | United Kingdom . |
| 1432978 | 4/1976 | United Kingdom . |
| 1509229 | 5/1978 | United Kingdom . |
| 1519172 | 7/1978 | United Kingdom . |
| 1535607 | 12/1978 | United Kingdom . |
| 2014046 | 8/1979 | United Kingdom . |
| 2028567 | 3/1980 | United Kingdom . |
| 1574498 | 9/1980 | United Kingdom . |
| 2047619 | 12/1980 | United Kingdom . |
| 2000079 | 1/1982 | United Kingdom . |
| 2023494 | 9/1982 | United Kingdom . |
| 2023068 | 11/1982 | United Kingdom . |
| 2055690 | 5/1983 | United Kingdom . |
| 2124907 | 2/1984 | United Kingdom . |
| 2087731 | 9/1984 | United Kingdom . |
| 2087240 | 9/1984 | United Kingdom . |
| 2087730 | 12/1984 | United Kingdom . |
| 2171915 | 9/1986 | United Kingdom . |
| 2186233 | 8/1987 | United Kingdom . |
| 2242348 | 10/1991 | United Kingdom . |
| 88/05269 | 7/1988 | WIPO . |
| 89/10084 | 11/1989 | WIPO . |
| 89/10109 | 11/1989 | WIPO . |
| 90/14061 | 11/1990 | WIPO . |
| 91/02643 | 3/1991 | WIPO . |
| 91/10415 | 7/1991 | WIPO . |
| 91/14414 | 10/1991 | WIPO . |
| 93/10300 | 5/1993 | WIPO . |

APPARATUS FOR MAKING FILM LAMINATED MATERIAL

This application is a continuation of application Ser. No. 07/973,145 entitled "APPARATUS FOR MAKING FILM LAMINATED MATERIAL (AS AMENDED)" and filed in the U.S. Patent and Trademark Office on Nov. 6, 1992, now U.S. Pat. No. 5,370,764. This application is related to application Ser. No. 08/289,039 entitled "METHOD FOR MAKING FILM LAMINATED MATERIAL" and filed in the U.S. Patent and Trademark Office on Aug. 11, 1994, which is a divisional of application Ser. No. 07/973,145.

BACKGROUND OF THE INVENTION

This invention generally relates to film laminated materials suitable for use in articles used to absorb, distribute and retain body liquids, such as sanitary napkins, catamenial pads, pantiliners, incontinence garments, disposable diapers and the like, and to a method and apparatus for making such articles. More specifically, this invention relates to a plastic film laminated material having improved liquid distribution and management and air circulation properties as well as enhanced comfort and softness when placed in contact with human skin.

Various nonwoven and film materials have been used as bodyside liners or covers in disposable absorbent articles. For example, U.S. Pat. Nos. 3,945,386, 3,965,906, 3,967,623, 3,994,299, 4,014,341, 4,323,069 and 4,324,246 disclose a combination of one or more nonwoven fibrous layers and a film layer containing apertures. Other patents, such as U.S. Pat. Nos. 3,888,254 and 4,675,013, disclose the use of a cover layer that is laminated to other fibrous layers. U.S. Pat. No. 4,762,520 discloses forming a bodyside liner from a carded fiber fabric containing melt fibers subdivided into parallel streaks. Other patents, such as U.S. Pat. Nos. 4,710,186, 4,755,413, 4,798,604 and 4,806,411 disclose forming apertures in the liner. U.S. Pat. No. 4,333,465 discloses a liner comprising a liquid-impermeable composite material having a liquid-permeable zone. Finally, U.S. Pat. Nos. 3,676,242, 4,690,679, 4,725,473 and 4,878,974 disclose various methods of making film and fiber composite liner materials by coextrusion, lamination and the like.

U.S. Pat. No. 5,137,600, and U.S. Ser. No. 07/633,594, filed on Dec. 21, 1990 by inventors C. Everhart et al., entitled "High Pulp Content Nonwoven Composite Fabric", both of which are assigned to Kimberly-Clark Corporation, relate to nonwoven webs that can be used in absorbent articles. Published Japanese Utility Model No. Hei 1[1989]-122727 discloses a sanitary napkin that has a liner constructed of two different hydrophobic materials, both of which contain apertures. U.S. Pat. No. 4,285,342 is somewhat similar, except instead of using two different materials, a large opening is formed in the liner of a diaper to enhance fluid flow into the absorbent core. U.K. patent 2,124,907 teaches a fabric bonded to a water-impermeable material, with both materials located on the bodyside surface of the absorbent article.

U.S. Pat. No. 4,908,026 discloses the use of a flow zone control layer located beneath the cover for facilitating dispersion of body liquids along the length of the absorbent article, before allowing the liquid to pass into the absorbent core. Other patents that disclose the use of a liquid transfer or a liquid distribution layer beneath the liner include U.S. Pat. Nos. 4,397,644, 4,480,000, 4,519,799 and 4,798,603. These patents disclose various materials and compositions for the transfer or distribution layer, which assist in directing the body exudates downward into the absorbent core.

Notwithstanding the development of the above-described materials, the need remains for a film laminate material that can provide improved liquid intake and distribution as well as air circulation when used as a body contacting layer in a disposable absorbent article, resulting in greater surface dryness and comfort for the wearer's skin.

SUMMARY OF THE INVENTION

This invention relates to a plastic film laminated material wherein a first film layer comprising a thin film of a thermoplastic material and a second nonwoven layer comprising a plurality of staple fibers or continuous filaments of one or more thermoplastic materials are bonded together in a spaced apart bonding pattern having apertures formed therein to form a film laminate having improved liquid distribution and management properties as well as enhanced surface dryness and comfort and softness when placed in contact with human skin. Also disclosed are a method and apparatus for making such a film laminate.

BRIEF DESCRIPTION OF THE DRAWINGS

The film laminated material of this invention will be better understood by reference to the following description of an embodiment of the invention taken in conjunction with the accompanying drawings.

FIGS. 3b and 3c are enlarged views of portions of the outer surfaces of the thermal bonding rolls of FIG. 3a;

FIG. 4b is a cross-sectional view of FIG. 4a;

FIG. 5b is a cross-sectional view of FIG. 5a;

DETAILED DESCRIPTION

The present invention comprehends a plastic film laminated fabric or material having a first layer comprising a thin film of a thermoplastic material and a second fibrous layer comprising a plurality of staple fibers or continuous filaments of one or more thermoplastic materials. The first layer and second layer, the latter of which can be a nonwoven web, are formed into a plastic film laminate by a spaced apart bonding pattern, such as by thermal bonding between a pair of heated embossing or bonding rolls having raised bonding patterns on the outer surfaces thereof. This spaced apart bonding pattern provides high structural integrity between the first and second layers without compromising the flexibility or surface texture of the first layer or the loftiness of the second layer. Apertures are formed in the spaced apart bonding areas to enhance liquid distribution and air circulation through the respective layers of the plastic film laminate into the absorbent core of the absorbent article. The plastic film laminate formed in accordance with the present invention exhibits improved liquid intake and distribution and air circulation characteristics, resulting in greater surface dryness and comfort when placed against human skin. The plastic film laminate of this invention further provides a lofty, pillowed structure that exhibits improved softness and cushiony feel to the user. Other attributes and advantages of the present invention will be apparent from the ensuing disclosure and appended claims.

As used herein, the terms "nonwoven web" and "nonwoven layer" mean a fibrous web or layer having a structure of individual fibers or filaments that are interlaid in a random pattern. Nonwoven webs have been formed in the past, as known to those of ordinary skill in the art, by a variety of processes, such as, for example, meltblowing, spunbonding, air-laying, wet-laying, dry-laying, dry staple and carded web processes. While nonwoven webs can be used in practicing the present invention, the invention is not to be considered limited to nonwoven materials and other suitable fibrous structures may be employed.

The plastic film laminated material of this invention will be described herein in connection with its use in disposable absorbent articles, however, it should be understood that potential applications of this invention need not be limited to such disposable absorbent articles. As used herein, the term "disposable absorbent article" means an article that is used to absorb and retain body exudates and is intended to be discarded after a limited period of use. Such articles can be placed against or in close proximity to the body of the wearer to absorb and retain various exudates discharged from the body.

Figure 1:
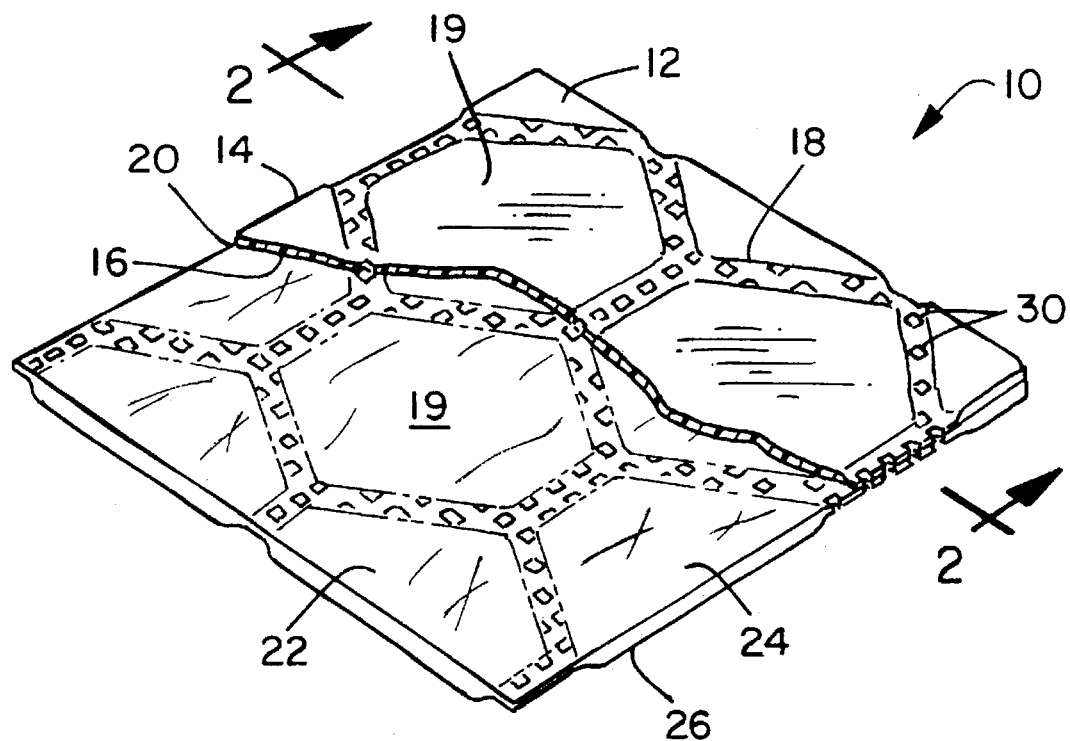
FIG. 1 is a perspective partial sectional view of a plastic film laminated material according to the present invention.

Referring now to FIG. 1, a perspective partial sectional view of an embodiment of the present invention is shown. The plastic film laminated material 10 comprises a first film layer 12 and a second nonwoven layer 22. The first layer 12 has an upper surface 14 and a lower surface 16 and the second layer 22 has an upper surface 24 and a lower surface 26. In the embodiment shown, a plurality of thermal fusion bonds in a spaced apart bonding pattern 18 extend through the thickness of the film laminated material 10 to thermally fuse or bond the plastic film material of the first layer 12 with fibers of second layer 22 at the interface 20 therebetween. Bonding of the first and second layers is substantially limited to the bonding regions 18. That is, in the areas 19 of the first and second layers outside of the bonding pattern 18, the respective layers are only lightly bonded to one another by fusing from thermal energy. Thus, the bonding regions 18 are separated or "spaced apart" by lightly bonded areas 19. Also as shown in this embodiment, apertures 30 are formed within the bonding areas 18 to improve the liquid distribution rate and air circulation of the film laminated material 10.

The first film layer 12 of the present invention may be formed of any suitable commercially available thin thermoplastic material, such as polyethylene, polypropylene, co-polymers and the like. The second fibrous layer of the present invention may be formed of any suitable natural or synthetic fibers in any appropriate structure, although in the embodiments shown in the accompanying drawings, these fibers are formed into a nonwoven layer. In general, the nonwoven second layer of the present invention can be prepared from noncontinuous fibers, continuous filaments or a combination thereof. The method of producing the nonwoven second layer in the embodiment shown employs dry staple processes, or more specifically, carded web techniques, as known to those of ordinary skill in the art. While carded web techniques can be advantageously employed in forming the nonwoven second layer of the present invention, spunbonding, meltblowing, air-laying and other techniques known to those of ordinary skill in the art that produce noncontinuous fibers and continuous filaments are also considered within the scope of this invention. Carded webs suitable for use in the practice of the present invention can have the fibers in an aligned or an unaligned configuration. Conventional carding machines, as known to those of ordinary skill in the art, can be employed in producing the nonwoven second layer of the present invention.

Commercially available thermoplastic polymeric materials can be advantageously employed in the second layer of the present invention. Examples of such polymers, by way of illustration only, include polyolefins, polyamides, polyesters and the like. The fibers may have any suitable morphology and may include hollow or core fibers, shaped fibers, bicomponent fibers or high absorbent particle impregnated fibers.

In the embodiment shown in FIG. 1, the first layer 12 of the film laminate 10 is a thin thermoplastic film, such as a catalloy polymer blend of about 62% polypropylene, about 30% polyethylene and about 7.5% titanium dioxide sold as XP-312 by Edison Plastics having offices in South Plainfield, N. J. (Another example of a suitable thermoplastic film having a higher tensile strength in the machine direction, as defined hereinbelow, is XP-113-0, also sold by Edison Plastics.) The second nonwoven layer 22 of the film laminated material 10 is a bonded, substantially unbonded or unbonded carded web made of a blend of polypropylene and polyester fibers. By "substantially unbonded" as used herein is meant a web with fibers that are sufficiently bonded together, by known bonding processes, for handling the web, but insufficiently bonded to provide the needed strength and integrity for the end-use application. By "unbonded" as used herein is meant a web with fibers that are not mechanically, thermally nor chemically bonded together.

The ratio of different thermoplastic fibers in the second layer 22 can be varied as appropriate for the intended end-use application of the film laminated material. For example, the ratio of polypropylene to polyester fibers by total weight of the second layer 22 can range from about 100:0 to about 25:75, with about 40:60 being the ratio for the embodiment shown.

It is an important advantage of the present invention that certain materials that might not have optimum properties in a nonwoven web for various reasons may be used in the present invention in combination with a thin plastic film to produce a better set of properties. For example, an unbonded or substantially unbonded nonwoven layer of polypropylene and polyester fibers may be considered too soft and weak for certain nonwoven web applications. However, in following the teachings of the present invention, a nonwoven layer made of an appropriate blend of polypropylene and polyester fibers can be bonded to a thin plastic film layer, such as a layer of polyethylene film, to thereby make a more desirable plastic film laminate.

The fiber sizes, basis weights and densities of the fibrous second layer of the film laminate 10 of the present invention also can be readily varied depending on the intended use of the film laminated material. For example, in one application of the present invention, the film laminated material can be used as a body facing liner or cover material for a disposable absorbent article having an absorbent core placed between the liner and an outer baffle. Such disposable articles include, by way of illustration only, sanitary napkins, diapers, training pants, incontinence garments and the like. For this application, the film layer 12 can be a thermoplastic film having a thickness of about 0.6 mil. The thermoplastic fibers in the second layer 22 can, but need not, be the same as the thermoplastic material of the first layer 12, however, nonwoven layer 22 must contain at least 40% thermoplastic fibers that have a common adhesion bond with the thermoplastic film of first layer 12.

The polypropylene fibers of second layer 22 can be as fine as about 1.0 denier (12.5 μm in diameter) to as coarse as about 3.0 denier (21.6 μm) and have crimped fiber length of from about 1.25 in. (31.75 mm) to about 2.5 in. (63.5 mm), although it is desirable for the polypropylene fibers to be from about 2 denier (17.6 μm) to about 2.2 denier (18.5 μm) and have a crimped fiber length of about 1.5 in. (38.1 mm). The polyester fibers in the second layer can be from about 3 denier (17.5 μm) to about 9 denier (30.4 μm) and have a crimped fiber length of from about 1.25 in. (31.75 mm) to about 3 in. (76.2 mm), with polyester fibers of 6 denier (24.8 μm) having a crimped fiber length of about 2 in. (50.8 mm) being suitable. (It is known in the art that crimping is a function of fiber type, diameter and density.) While not wishing to be bound by any particular theory, it is currently believed that the use of different fibers enhances the liquid wicking and distribution properties of the second layer 22. The fibers in the second layer 22, which have different diameters, tend to form pores of varying sizes in multiple planes. The differing pore sizes in multiple planes in second layer 22 are believed to enhance wicking of liquid throughout the second layer 22 and liquid intake into and distribution through the second layer 22. It is further currently believed that the resiliency of the polyester fibers is a contributing factor to the improved liquid management and air circulation characteristics of the film laminate of this invention. Consequently, in this application, the second layer 22 functions as a surge layer or temporary reservoir for the liquid passing through the film laminated material 10 into the absorbent core of an absorbent article.

The film laminated material 10 of this invention can have a basis weight of from about 42 g/m² (1.18 oz/yd²) to about 46 g/m² (1.29 oz/yd²), a thickness of from about 0.037 in. (0.940 mm) to about 0.043 in. (1.092 mm) and a density of from about 0.042 g/cc to about 0.045 g/cc. Density is determined using the following equation:

$$\frac{\text{Basis Weight (g/m}^2\text{)} \times 0.0000394}{\text{Thickness (in.)}} = \text{Density (g/cc)}$$

For example, in the embodiment shown, the basis weight for the film laminate 10 is about 44.1 g/m² (1.23 oz/yd²) the thickness is about 0.040 in. (1.016 mm) and the density is about 0.043 g/cc.

The basis weight of the film laminated material 10 was measured using a device that measures the weight of a sample of the nonwoven material. Each sample measured no less than 4 in² (2580 mm²). Each sample was cut, smoothed to eliminate folds or wrinkles, and weighed on an analytical balance to the nearest 0.01 g. The basis weight then was calculated by dividing the sample weight by the sample area.

The thickness of the film laminated material 10 was measured using a device that applies a constant loading pressure of 0.05 psi (35.15 kg/m²) to a sample of the film laminated material. Each sample measured at least 5×5 in. (127×127 mm). Each sample was cut out, smoothed to eliminate folds or wrinkles, placed under a circular plexiglass platen (foot) having a 3 in. (76.2 mm) diameter, centered as much as possible, and the platen then was lowered onto the specimen. The thickness of each sample was recorded to the nearest 0.001 in. (0.0254 mm).

In the embodiment shown, the basis weight for the second layer can range from about 0.7 oz/yd² (24 g/m²) to about 1.02 oz/yd² (35 g/m²), with about 0.9 oz/yd² (32 g/m²) being desireable. The density for the second layer can range from about 0.024 g/cc to about 0.045 g/cc, with about 0.035 g/cc being desireable.

Figure 2:
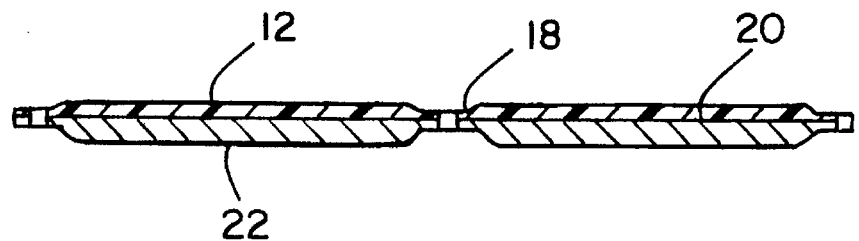
FIG. 2 is a cross-sectional elevational view of the plastic film laminated material of FIG. 1 taken along line A—A of FIG. 1.

Referring now to FIG. 2, a cross-sectional view of the embodiment of the film laminate material 10 of the present invention described above is shown, comprising a first plastic film layer 12 and a second nonwoven layer 22. A series of bonds forming a spaced apart bonding pattern 18 extend through the thicknesses of the respective layers and bond the first layer 12 to the second layer 22 at the interface 20 in the bonding regions 18. The manner of forming the spaced apart bonding pattern 18 now will be described.

The spaced apart bonding regions 18 may be produced by any suitable method of bonding the respective first and second layers to one another at the interface 20 therebetween that yields a film laminated material 10 having the liquid management, air circulation and other properties described herein. Thermal bonding, which includes the use of a pair of heated embossing rolls, is considered a useful method of forming the bonding pattern 18, as described in greater detail hereinbelow.

The present invention contemplates bonding of the respective layers in various sequences. For example, the second layer 22 may be formed in a first operation and then bonded to the first layer 12 in a second operation. Alternatively, the second layer 22 may be formed in a first operation, with the fibers of the second layer 22 bonded in a second operation, and the respective layers bonded together in still another separate operation. The thermoplastic fibers of second layer 22, which can be initially unbonded or substantially unbonded, do have a degree of thermal bonding when formed into the film laminated material 10, as further described below.

In the embodiment shown, for example, second layer 22 may be thermobonded by passing the layer 22 between a pair of bonding rolls of conventional construction (i.e., an engraving roll and a smooth roll) heated to a temperature of between 270° F. (132° C.) and 300° F. (149° C.), with 275° F. (135° C.) to 285° F. (141° C.) being desireable. The appropriate temperature for bonding layer 22 using thermal bonding rolls will vary depending upon the rotational surface speeds and diameters of the bonding rolls and the thermoplastic fibers used. The second layer 12 may alternatively be bonded by other known bonding processes, such as by pattern adhesive bonding, needling or hydro or airjet entangling of the fibers.

The degree of bonding of the first layer 12 to the second layer 22 may be controlled in the spaced apart bonding region 18 by altering the percent bond area, which refers to the surface area of the interface between the respective layers that is occupied by bonds within the bonding regions.

Thus, as shown in FIGS. 1 and 2, the interface 20 of the first layer 12 and second layer 22 has a spaced apart pattern of bonds 18 disposed across its surface and the ratio of the surface area occupied by the bonding regions 18 to the total area of the surface of the interface 20 is the percent bond area for the interface 20. In the embodiment shown, the percent bond area of the film laminate can range from about 1% to about 6%, with about 2% to about 4% being desireable. While a hexagonal (honeycomb-like) bonding pattern is shown in this embodiment, the present invention encompasses other geometric, non-geometric, repeating and non-repeating bonding patterns, which are suitable for incorporation into the film laminated material of the present invention.

Figure 3:
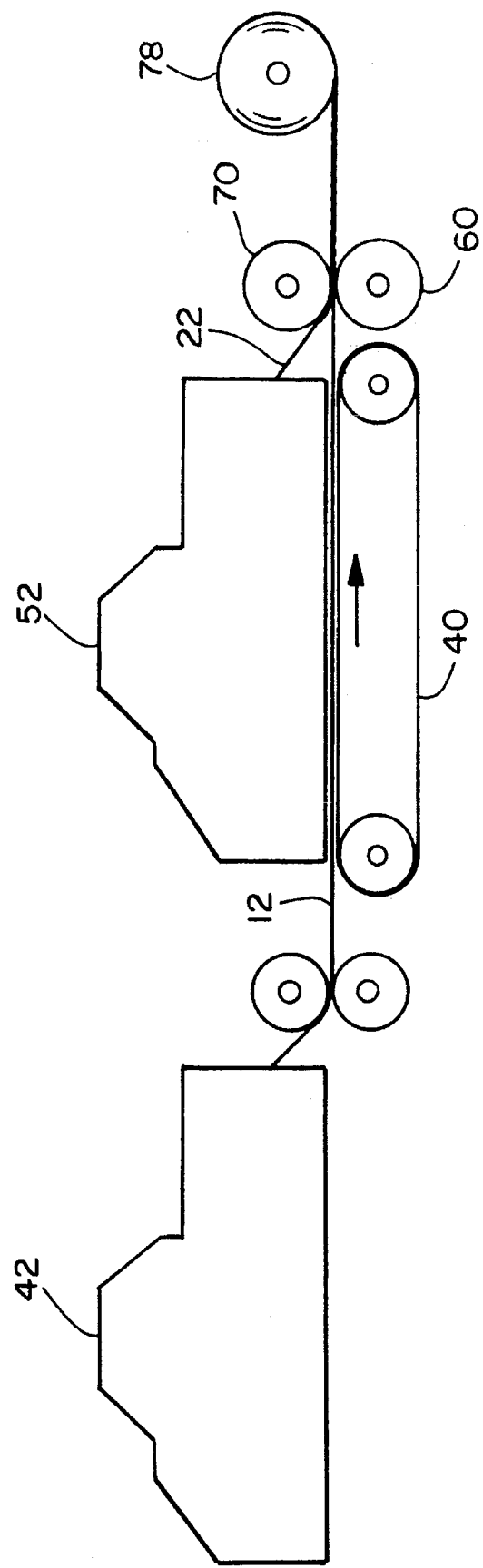
FIG. 3 is a schematic diagram showing process apparatus for forming a plastic film laminated material in accordance with the present invention.

FIG. 3 is a schematic diagram of the apparatus used for forming the above-described embodiment of the film laminated material of the present invention. As stated above, conventional carding machines, such as described in U.S. Pat. Nos. 3,604,062 and 3,604,475, can be employed in producing the nonwoven second layer of the present invention. As shown, the first layer 12 is unwound from a roll 42 onto a moving belt 40, while carding machine 52 lays down the second layer 22 on top of the first layer 12. In this way, first layer 12 acts as a base substrate for second layer 22 as the two layers pass through the forming process.

Optionally, the second layer 22 may be passed through a pair of compacting rollers that slightly compact the fibrous web to thereby increase the integrity of the web and to aid in further processing. Second layer 22 also may be passed through apparatus that orients the fibers in the web to optimize material strength in the machine direction (MD) and cross direction (CD). As used herein, machine direction (MD) refers to the direction in which the web was laid down (from left to right in FIG. 3) and cross direction (CD) refers to the axis perpendicular to the direction in which the web was laid down. MD strength for the film laminate of this invention must be sufficiently high (at least about 400 g/in. (15.7 g/mm) to about 1,000 g/in. (39.4 g/mm), with about 450 g/in. (17.7 g/mm) to about 700 g/in. (27.6 g/mm) being desireable) so that the film laminated material will not be broken during high speed manufacturing processes used for producing disposable absorbent articles, such as sanitary napkins.

The two layers next pass through the two bonding rolls 60 and 70. In the embodiment shown in FIGS. 3 and 3a, both bonding rolls are heated and have raised (male) bonding patterns on the outer surfaces thereof. The lower roll 60 has a spaced apart bonding pattern 62 on its surface, while the upper roll 70 has raised bonding points 72 on its surface. In alternative embodiments, the positions of the bonding rolls can be reversed. It is a feature of this invention, therefore, that thermal bonding rolls having different male or raised bonding patterns on each of the outer surfaces thereof are employed to create a spaced apart bonding pattern for bonding together the respective layers of the film laminated material.

As the two layers 12 and 22 pass between these two heated rolls 60 and 70, each layer becomes stabilized by the formation of discrete compacted bonding areas 18 of thermally induced bonds that extend through a major portion of the thickness of each layer. The thickness of the compacted or bonded regions 18, which may vary depending upon the thicknesses of the respective layers 12 and 22, can range from about 50 μm to about 150 μm, with about 70 μm to about 110 μm being used in the embodiment shown herein. The compacted bonded areas of film laminated material 10 are distributed in a bonding pattern 18 formed by the points of contact between the raised bonding patterns on the two heated rolls 60 and 70, with lightly bonded fiber spans 19 therebetween.

Figure 6:
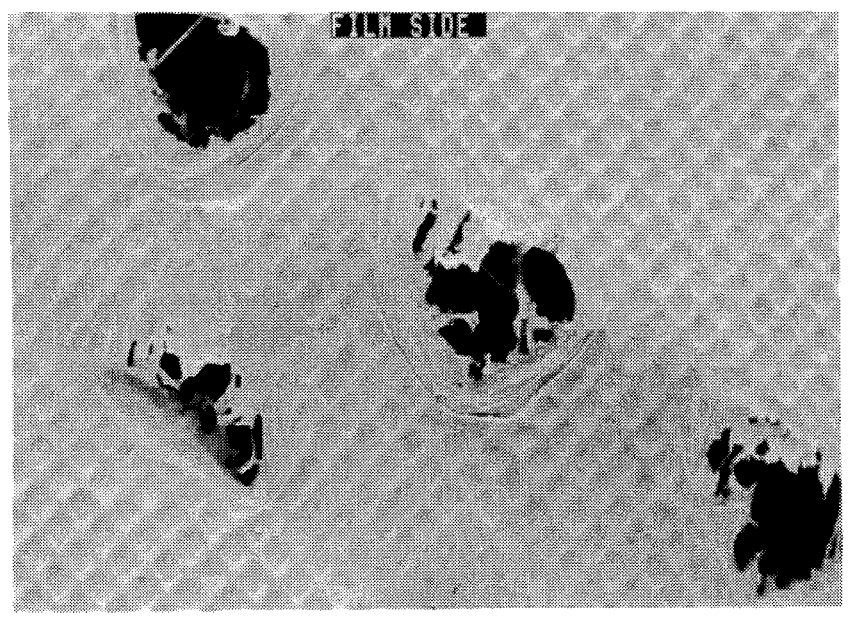
FIG. 6 is a photomicrograph (28.7 magnification, 12 mm working distance, 5 KV accelerating voltage) of a portion of the apertured bonding region of the film laminated material of the present invention, with the film layer of the film laminated material facing the viewer.
Figure 7:
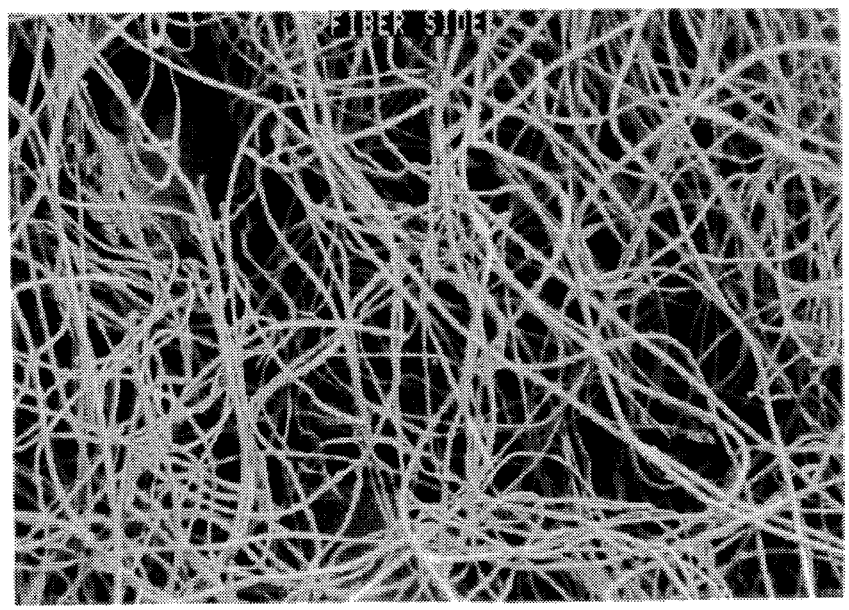
FIG. 7 is a photomicrograph (28.7 magnification, 12 mm working distance, 5 KV accelerating voltage) of a portion of the apertured bonding region of the film laminated material of the present invention, with the nonwoven layer of the film laminated material facing the viewer.

Apertures 30 are formed in the bonded areas 18 formed by the points of contact between the raised patterns on the heated bonding rolls 60 and 70, as described in greater detail below. While the exact size and shape of the apertures 30 are not considered critical by the inventor (see FIGS. 6 and 7), apertures having average diameters ranging from about 8 μm to about 580 μm or more can be advantageously employed in the present invention, with aperture average diameters from about 29 μm to about 277 μm being desireable. The apertures 30 are substantially free of film material throughout the thickness of the film laminated material 10 and provide a non-tortuous pathway for liquid to pass through the film laminated material 10. The apertures 30, consequently, allow rapid liquid intake through the first layer 12 into the second layer 22 and finally into the absorbent core of an absorbent article. It has been observed that liquid primarily flows away from the point of contact with the film material 10 along the apertured bonding regions 18, which act as channels for the liquid. The apertures 30 are to be distinguished from the pores formed between fibers in layer 22, which are not sufficiently large nor non-tortuous to allow such rapid liquid intake and distribution. Consequently, a film laminated material 10 is shown having spaced apart bonded areas 18 with lightly bonded areas 19 therebetween and apertures 30 formed in the bonded areas 18.

Two parameters of concern in regard to the specific combination of raised patterns on the bonding rolls that are used are the size of the raised bonding areas of the bonding rolls and the distance or spacing separating the bonding areas. These two parameters together affect the percentage of area on the film laminated material 10 that becomes bonded, as described above. It is important that the percent bond area be great enough to insure sufficient integrity of the film laminate for its intended use. On the other hand, it is important that the percent bond area not be too great, as a higher percent bond area usually produces a film laminate with reduced softness. The percent bond area of the lower roll 60 (the ratio of the surface area of the raised bonding pattern 62 to the total area of the outer surface of lower roll 60) of this embodiment can range from about 9% to about 20%, with about 18% to about 19.5% being desireable. The percent bond area of the upper roll 70 (the ratio of the surface area of the raised bonding points 72 to the total area of the outer surface of lower roll 70) of this embodiment can range from about 10% to about 30%, with about 11% to about 20% being desireable. As noted above, the percent bond area of the film laminate 10, which is the mathematical product of the percent bond areas of the upper roll 70 and lower roll 60, can range from about 1% to about 6%, with about 2% to about 4% being desireable.

It is further important that the raised bonding patterns of the two bonding rolls be combined to optimize the number of apertures within the bonded areas. In the embodiment shown in FIGS. 3a, 3b and 3c, the width of the raised bonding pattern 62 on the outer surface 64 of the lower roll 60 can range from about 0.04 in. (1.0 mm.) to about 0.08 in. (2.0 mm.), with a width of about 0.07 in. (1.8 mm.) being desireable, and the width at the base 66 of the raised bonding pattern 62 can range from about 0.06 in. (1.6 mm.) to about 0.12 in. (3.1 mm.), with about 0.11 in. (2.8 mm.) being desireable. The raised bonding pattern 62 of the lower roll 60 in this embodiment has an engraving depth of about 0.04 in. (1.0 mm), which is the distance between the outer surface 64 and base 66 of the raised bonding pattern 62. The individual hexagons 68 of the raised bonding pattern 62 of lower roll 60 can have a repeating width W of from about 0.65 in. (16.50 mm.) to about 0.68 in. (17.33 mm.), a repeating height H of from about 1.10 in. (28 mm.) to about 1.18 in. (30 mm.), and a pitch P of about 0.65 in. (16.50 mm.) to about 0.68 in. (17.33 mm.) at a pitch angle of from about 45° to about 60°.

Figure 3A:
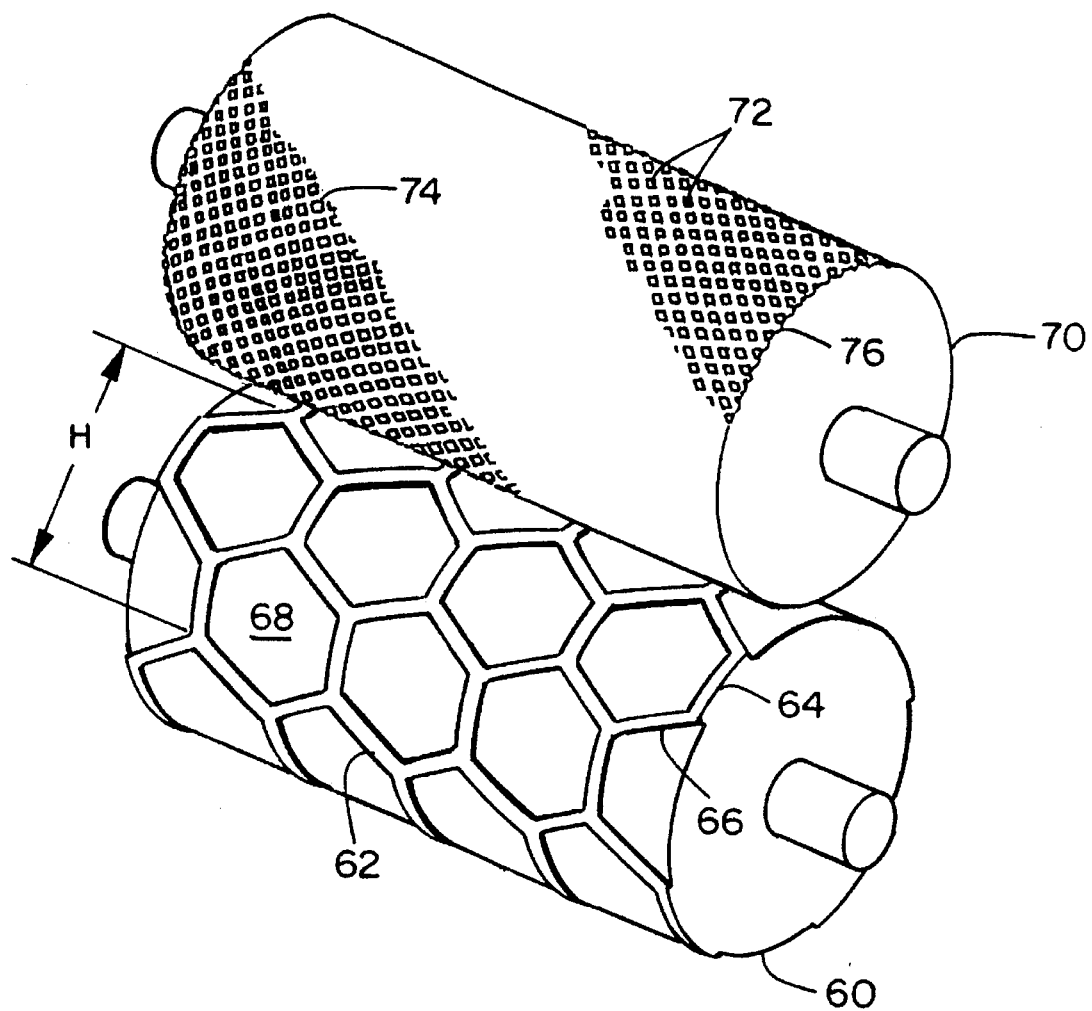
FIG. 3a is a perspective view of thermal bonding rolls for forming a plastic film laminated material in accordance with the present invention.
Figure 3B:
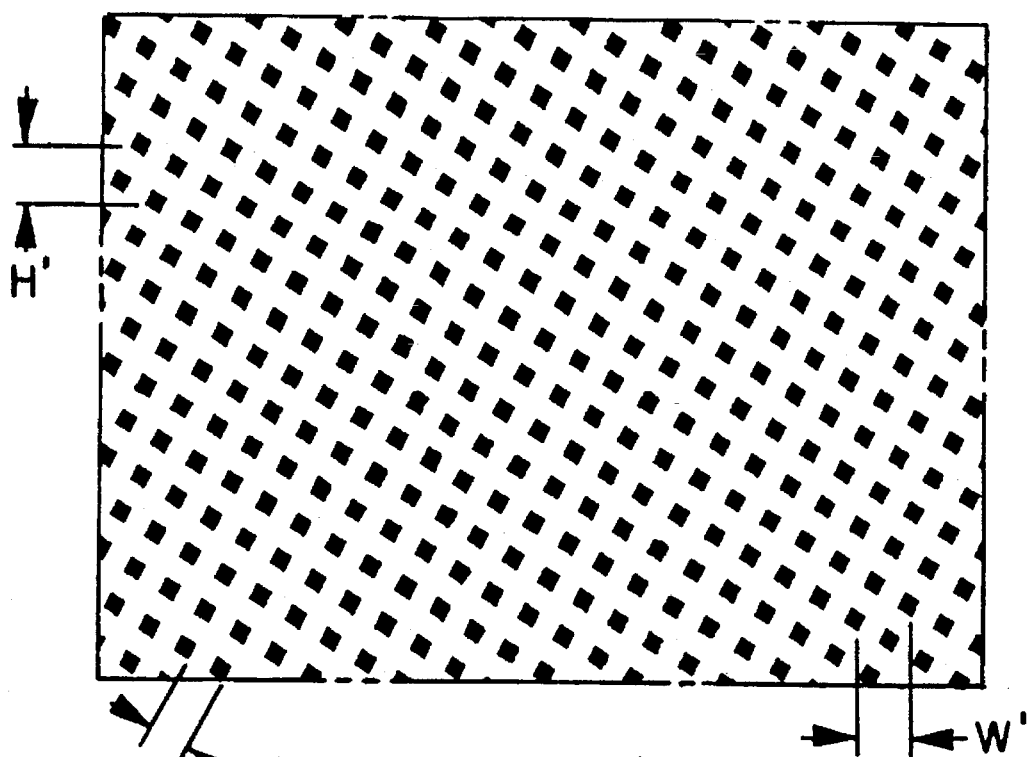
Figure 3C:
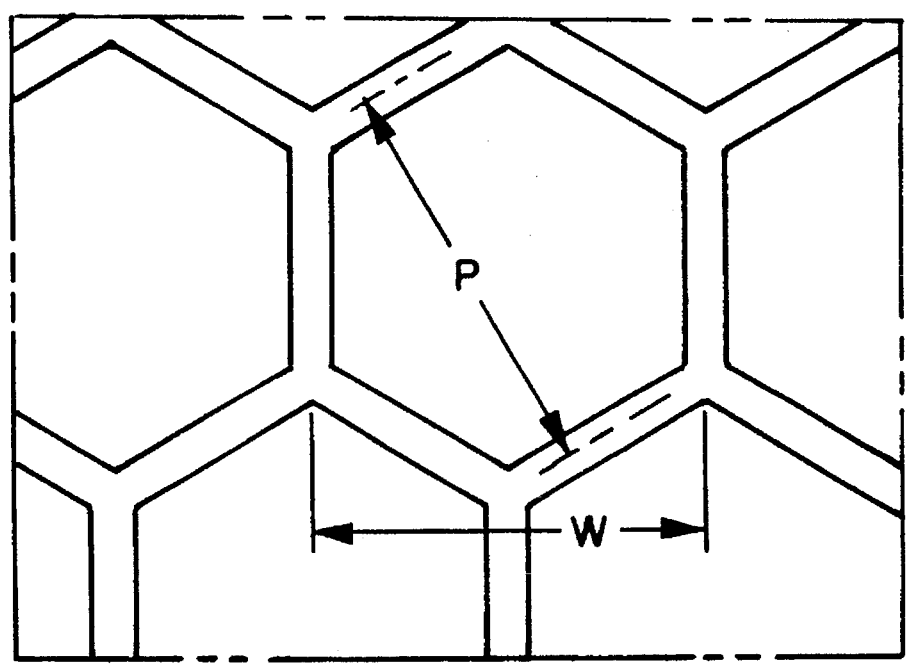

Still referring to FIGS. 3a, 3b and 3c, the width of the raised bonding points 72 on the outer surface 74 of the upper roll 70 can range from about 0.028 in. (0.70 mm) to about 0.031 in. (0.80 mm), with a width of about 0.030 in. (0.75 mm) being suitable. As is conventional in the art, the width at the base 76 of the raised bonding points 72 is slightly greater than the width on the outer surface 74. The raised bonding points 72 of the upper roll 70 can have an engraving depth of about 0.026 in. (0.65 mm). The individual raised bonding points 72 in this embodiment are arranged at about 218.0 bonding points/in$^2$ (33.8 bonding points/cm$^2$) and have a repeating width W' of about 0.094 in. (2.4 mm) to about 0.118 in. (3.0 mm), a repeating height H' of about 0.068 in. (1.72 mm), and a pitch P' of about 0.068 in. (1.72 mm) at a pitch angle of from about 30° to about 45°. While in the embodiment shown, the outer surface 74 of the raised bonding points 72 is in the form of a square, other geometric and non-geometric shapes may be employed as the raised bonding points 72 of upper roll 70.

The inventor has observed in optimizing the film laminated material 10 of the present invention, the following factors are interrelated:

1) Temperature of bonding rolls 60 and 70;
2) Line speed of the forming process;
3) Nip pressure between the bonding rolls;
4) Diameter of the bonding rolls; and
5) Types of materials used in forming layers 12 and 22. That is, modifying one or more of the above factors tends to affect the remaining factors as well. For example, an increase in the line speed of the forming process results in the layers of the film laminate being in contact with the bonding rolls for a shorter period of time. Consequently, the temperature of the bonding rolls may have to be increased to achieve the required degree of bonding of the two layers, thereby compensating for the change in line speed.

As noted above, an important factor relating to the bonding of the two layers is the temperature at which the bonding rolls 60 and 70 are maintained. Naturally, temperatures below a certain point for each polymer will not effect any bonding, while temperatures above another point will melt too much of the film and/or fibers. Also, its has been observed that the temperature of the bonding rolls can affect both the tensile strength and softness of the film laminate produced. In particular, within a certain range, higher temperatures will produce a film laminate with higher tensile strength. However, these same higher temperatures can produce a film laminate with decreased softness. This is likely due to a higher and lower degree of bonding that occurs within this range of temperatures. That is, the higher temperatures likely result in more and stronger interfilament bonding that is beneficial to tensile strength and somewhat detrimental to softness. In addition, higher temperatures likely result in a less lofty, pillowed structure, as the thermoplastic fibers in nonwoven layer 22 experience more shrinkage, adversely affecting the softness and cushiony feel of the film laminate material 10.

It has further been observed that the temperature of the rolls can affect the formation of apertures in the bonded areas of the web. While the apertures formed in the bonded areas are not solely thermally produced, thermal bonding allows the respective layers to be compressed to a sufficient degree that mechanical aperturing may occur, as further described below.

In the embodiment shown, the bonding temperature for lower roll 60 can range from about 150° F. (66° C.) to about 200° F. (93° C.), with a temperature of about 170° F. (77° C.) to about 180° F. (82° C.) being desireable, and the bonding temperature for upper roll 70 can range from about 190° F. (88° C.) to about 225° F. (107° C.), with a temperature of about 200° F. (93° C.) to about 210° F. (99° C.) being desireable. It is important that the bonding roll that contacts the first plastic film layer 12, which in this embodiment is lower bonding roll 60, has a lower temperature than the bonding roll that contacts the second nonwoven layer 22, which in this embodiment is upper roll 70, such that the softness and structural integrity of the first layer 12 is not significantly reduced, while the thermoplastic fibers in the second layer 22 are sufficiently heated to thermally fuse with the thermoplastic film in the first layer 12. In any event, the temperature of the bonding roll that contacts film layer 12 must be below the melting point of the film material employed.

Another important factor relating to the bonding of the two layers as well as the formation of apertures in the bonding regions is the line speed at which the respective bonding rolls are operated. In the embodiments shown, the rolls can operate at line speeds ranging from about 40 feet/min. (12 m/min.) to about 328 feet/min. (100 m/min.) or more. It has further been observed that aperture formation within the bonding regions can be significantly improved by employing different rotational surface speeds for the two bonding rolls. The difference in rotational surface speeds can differ from about 4% to about 20%, with about 5% to about 15% being conveniently employed. Either bonding roll may be employed with a higher rotational speed than the other bonding roll. While not wishing to be bound by any particular theory, it is believed that aperture formation is improved by operating the bonding rolls at different rotational speeds because the shearing forces tangential to the bonding roll surfaces in the thermally produced compacted bonding areas tear (mechanical aperturing) the film and fibrous materials at the points of contact between the raised bonding patterns of the bonding rolls.

Another important factor relating to the bonding of the two layers is the diameter of each bonding roll. While in the embodiment shown (and in the ensuing Examples), the bonding rolls each are about 12 inches (305 mm) in diameter, bonding rolls having smaller or larger diameters are suitable for producing the plastic film laminate of the present invention. Moreover, the diameters of the bonding rolls need not be identical.

Another important factor relating to the bonding of the two layers and aperture formation within the bonding regions is the nip pressure between the bonding rolls. In the embodiment shown, the bonding rolls produce a nip pressure of from about 60 pli (10 kg/1 cm) to about 400 pli (67 kg/1 cm), with a nip pressure of about 300 pli (50 kg/1 cm) being advantageously employed. It is likely that higher nip pressures will result in a less lofty, pillowed structure, adversely affecting the softness characteristics of the film laminated material 10.

In the embodiment shown, after the layers 12 and 22 of film laminated material 10 are bonded by bonding rolls 60 and 70, film laminated material 10 is wound on a take up roll (winder) 78. Alternatively, it may be desirable to design this apparatus to connect with a fabrication line for the end product. Higher tension on the take up roll 78 or fabrication line is another factor that is likely to adversely affect the loftiness of the film laminated material 10 of this invention.

Figure 4A:
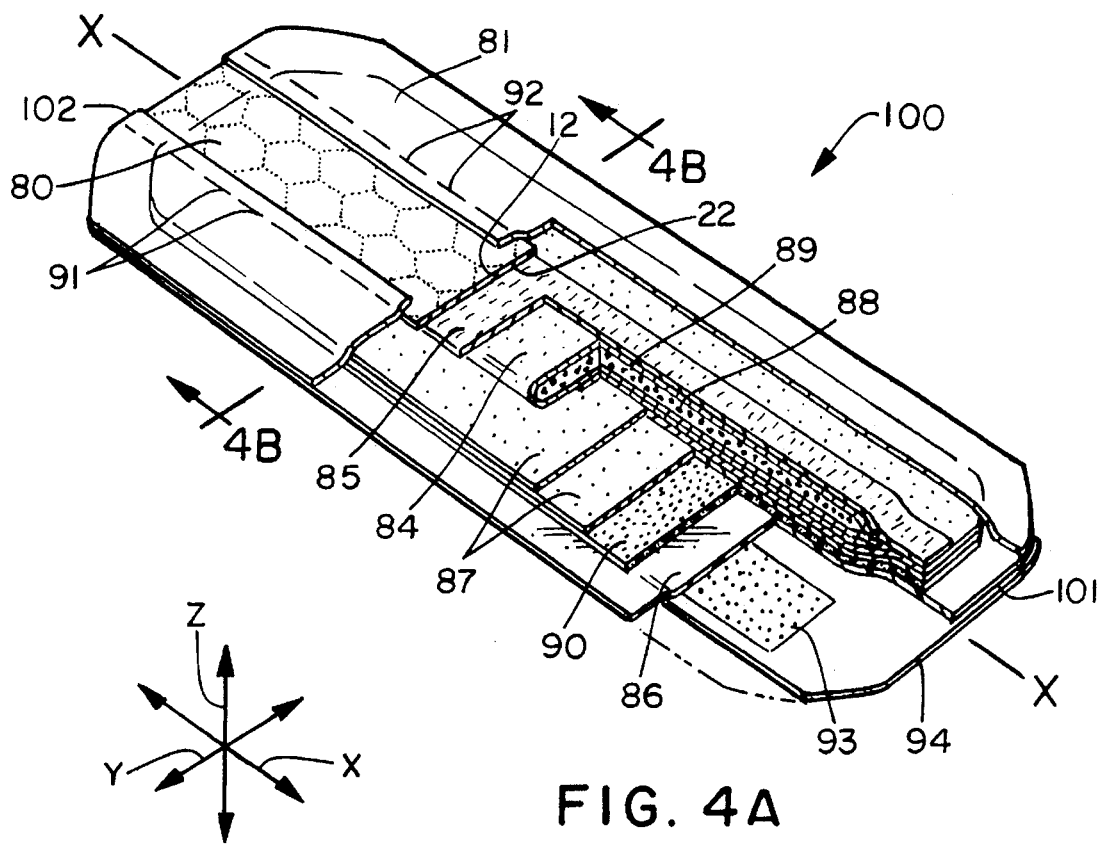
FIG. 4a is a perspective view of a disposable sanitary napkin including the plastic film laminated material of the present invention positioned on the side of the napkin that will be placed next to the wearer's body.
Figure 4B:
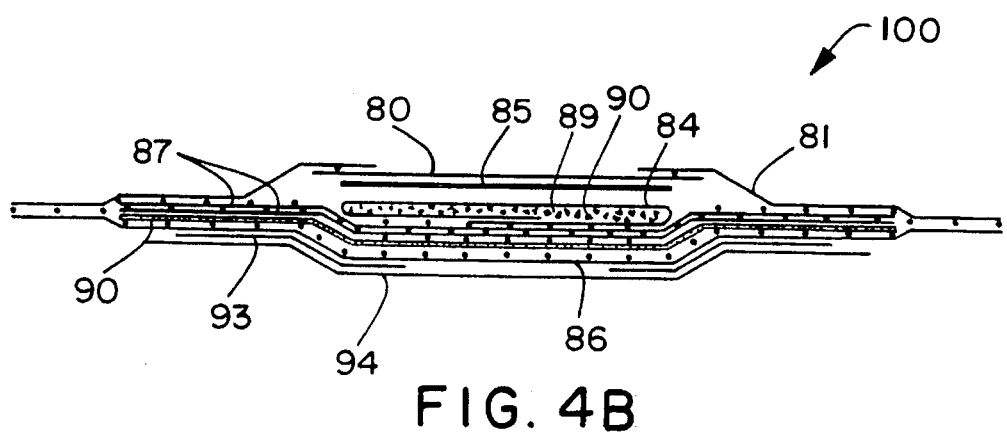

FIGS. 4a and 4b are a perspective view and a cross-sectional view, respectively, of a sanitary napkin 100, similar to that sold under the New Freedom® Ultrathin Maxi Pad trademark by the present assignee, except it includes the film laminated material of the present invention positioned on the side of the sanitary napkin that will be placed next to the wearer's body. Sanitary napkin 100 is an elongated member with distally spaced ends 101 and 102 and has a longer length than width. The length extends along the x axis, the width extends along the y axis and the thickness extends along the z axis. The particular shape of sanitary napkin 100 can vary, with the most common profiles being a narrow rectangular shape, an hourglass shape, an oval shape or a racetrack shape as shown in FIG. 4a.

In the embodiment shown, the sanitary napkin has a multi-layered construction. The sanitary napkin 100 includes a liquid-permeable dual component cover 82, a liquid-impermeable baffle 86 and a transfer layer 85 and an absorbent structure 84 positioned therebetween. The dual component cover 82 is secured or bonded to the baffle 86 to completely enclose transfer layer 85 and absorbent structure 84. Dual component cover 82 is designed to be positioned against the wearer's body, while the baffle 86 is positioned adjacent to an undergarment. Transfer layer 85 is positioned between dual component cover 82 and the upper surface of absorbent structure 84. Transfer layer 85 is aligned along the longitudinal central axis x—x.

Transfer layer 85 can have a single or multiple layer construction. When a single layer construction is used, as shown in FIGS. 4a and 4b, transfer layer 85 can be constructed of spunbond nonwoven material and direct body liquid downward (z-direction) into absorbent core 84, as well as in the x and/or y direction, if desired. Such a single layer transfer layer 85 also can be constructed of, for example, bonded carded web. In a multiple layer configuration (not shown), transfer layer 85 can have two vertically aligned portions or layers positioned along the longitudinal central axis x—x. The upper portion is in intimate contact with a portion of dual component cover 82 and can be a material such as spunbonded or bonded carded web. The upper portion primarily directs the body liquid downward, in the z-direction, into the lower portion. The lower portion can be a material such as woodpulp fluff, coform, tissue or meltblown. The lower portion primarily directs the body liquid outward, in the x- and y-directions. The body liquid is thereby dispersed across a larger surface area of absorbent structure 84, and this can reduce the amount of time needed for absorbent structure 84 to take up or receive the liquid. This ability to rapidly transfer body liquid downward away from dual component cover 82 assists in maintaining a dry cover adjacent the user's body.

Transfer layer 85 can be an elongated strip having a thickness of less than about 3 mm, with between about 0.1 mm about 1.5 mm being desireable. The density of separation layer 85 can vary depending upon the end use application, with a density of about 0.95 oz/yd$^2$ (33.8 g/m$^2$) being suitable for the embodiment shown. Transfer layer 85 can be of varying lengths and widths. The length can be greater than, equal to or less than the length of absorbent core 84. Generally, for sanitary napkins, the length should be at least 50% of the length of absorbent core 84. The width of transfer layer 85 can range from between about 0.25 in. (6 mm) to about 3.0 in. (76.3 mm), with about 0.75 in. (19 mm) to about 2.5 in. (64 mm) being desireable and about 1.0 in. (25.4 mm) to about 2.0 in. (50.8 mm) being particularly useful.

Absorbent structure 84 includes an absorbent laminate constructed of a hydrophilic material 89 and a superabsorbent material 88. The hydrophilic material 89 can be made from natural or synthetic fibers, including cellulose fibers, surfactant-treated meltblown fibers, wood pulp fibers, regenerated cellulose or cotton fibers, or coform, which is a blend of pulp and synthetic meltblown fibers. A hydrocolloidal material 88, commonly referred to as a superabsorbent, is added to the hydrophilic material to increase absorbency and retention of body liquid. As used herein, the term "superabsorbent" refers to a material, natural or synthetic, capable of absorbing or gelling at least about 10 times its weight in liquid. As shown is FIGS. 4a and 4b, absorbent structure 84 includes a laminate structure in which the hydrophilic material 89 (Airtex 395 from Fiberweb North America, Inc.) is e-folded and the superabsorbent 88 (Favor SAB-835 from Stockhausen, Inc.) is evenly distributed therein. A hot melt adhesive (or other known bonding means) can be used to adhere the superabsorbent 88 to the hydrophilic material 89.

The absorbent structure 84 also includes one or more tissue layers 87, which are placed below the absorbent laminate. The lowermost surface of the tissue layers 87 is bonded to a foam backing layer 90. Additional tissue layers 87 (not shown) can be placed above the absorbent laminate, with the upper surface of the tissue layer 87 bonded by construction adhesive (or other known bonding means) to the second material 81 of dual component cover 82.

Foam layer 90 can be of varying lengths and widths. The length and width can be, as in the embodiment shown, equal to the length and width of tissue layer 87. Foam layer 90 can be constructed of, for example, polyethylene, as in the embodiment shown. The lower surface of foam layer 90 is bonded to outer baffle 86.

Liquid-impermeable outer baffle 86 functions to prevent body liquids, absorbed by the absorbent structure 84, from leaking out and soiling or staining an adjacent undergarment. Liquid impermeable baffle 86 can be made from a micro-embossed polymeric film, such as polyethylene or polypropylene, or it can be made from bicomponent films. In the embodiment shown, baffle 86 is formed of 1 mil polyethylene.

As shown in FIGS. 4a and 4b, dual component cover 82 is constructed of two different and distinct materials 80 and 81. Film laminated material 80 forms a body facing outer layer 12 comprising a thin thermoplastic film and an inner layer 22 comprising a bonded, substantially unbonded or unbonded carded web formed of a blend of polypropylene and polyester fibers as described above. Film laminated material 80 is positioned about the longitudinal central axis x—x of the sanitary napkin 100 and constitutes the primary liquid-receiving region of the dual component cover 82. The sanitary napkin 100 is positioned adjacent to the human body such that the principal point of discharge of body liquid or excrement is in direct alignment with the outer layer 12 of film laminated material 80.

The film laminated material 80 can be of varying lengths and widths and can have various shapes. As shown in FIG. 4a, film laminated material 80 has a rectangular shape and a length equal to the length of the sanitary napkin 100. Other shapes and lengths less than the length of the entire sanitary napkin also may be suitable. The width of film laminated material 80 can vary from about 0.25 in. (6.4 mm) to about 3.0 in. (76.2 mm), with a width of about 1.0 in. (25.4 mm) to about 2.0 in. (50.8 mm) being suitable. Generally, for feminine care products, a width of about 25% to about 100% of the absorbent article is acceptable. In the embodiment shown in FIGS. 4a and 4b, the film laminated material 80 forms a smaller portion of the exposed surface area of the dual component cover 82 than the second material 81. The film laminated material 80 may, however, form an equal or larger portion of the dual component cover 82, if desired.

The second material 81 of the dual component cover 82 may be a liquid-permeable nonwoven web. The nonwoven web can be a fibrous material formed from fusible polymeric fibers or filaments. The nonwoven web 81 shown is non-perforated, although a perforated web can be used if desired. Polypropylene spunbond material, bonded carded webs, thermally bonded carded webs, spunbonded webs of bicomponent fibers and bonded carded webs of bicomponent fibers are suitable. The nonwoven web can be formed from any of the following polymers: polyesters, polyolefins and the like. In particular, polypropylene spunbond and bonded carded webs are suitable materials. An appropriate nonwoven web material should have a uniform web with a denier of about 1.0 or greater. Such a material, commonly referred to as a linear drawn spunbond, is described in U.S. Pat. No. 4,340,563 issued to Appel et al., the disclosure of which is hereby incorporated by reference.

In FIGS. 4a and 4b, the second material 81 overlaps a portion of the longitudinal side edges of the film laminated material 80 and is bonded along lines 91 and 92. The second material 81 can be bonded to the film laminated material 80 by a mechanical attachment, an adhesive, an ultrasonic bond, a thermal bond, a pressure bond or a combination of both heat and pressure. Other known means of attaching the two materials 80 and 81 together can also be used. Bonding of these two materials 80 and 81 together is not required in all cases, however. Dual component cover 82 can be constructed off-line and then assembled into a sanitary napkin 100, or it can be constructed on-line.

Second material 81 is secured to film laminated material 80 and forms a secondary liquid-receiving region of dual component cover 82. Second material 81 is spaced away from the principal point of discharge of body liquid which the sanitary napkin 100 is designed to receive. Although second material 81 is intended as the secondary liquid-receiving region of dual component cover 82, it still has the ability to allow liquid to pass down through it and into the absorbent core 84. The absorbency rate of second material 81, which is defined as the amount of time it takes a material to absorb a certain quantity of liquid, is about equal to or less than the absorbency rate of film laminated material 80. Accordingly, most of the body liquid, under normal conditions, is intended to pass down into the absorbent core 84 through film laminated material 80.

In the embodiment shown, transfer layer 85 is not bonded directly to film laminated material 80 nor to the top surface of absorbent structure 84, although second material 81 is bonded by construction adhesive to the top surface of absorbent structure 84. Securing second material 81 directly to absorbent structure 84 can improve the dryness of the entire cover and assist in preventing rewetting.

At least one garment adhesive strip 93 may be secured to an exterior surface of the baffle 86. A removable peel strip 94 is positioned over the adhesive strip 93 and is designed to be removed by the user before the sanitary napkin is attached to the interior surface of an undergarment.

In alternative configurations (not shown), film laminated material 80 and second material 81 need not be bonded together. For example, film laminate material 80 and second material 81 may be adhesively bonded to the top surface of absorbent core 84, which can improve liquid transfer into the absorbent core, increase the dryness of the entire cover 82 and assist in preventing rewetting.

Optionally, the cover 82 of the sanitary napkin can be constructed solely of the film laminated material 80. Thus, film laminated material 80 would have an appropriate length, width and overall shape to allow it to be secured to the periphery of the baffle 86 and completely enclose the absorbent structure 84 and transfer layer 85. Certain efficiencies in manufacturing, as well as performance improvements, can be achieved by this configuration.

Figure 5A:
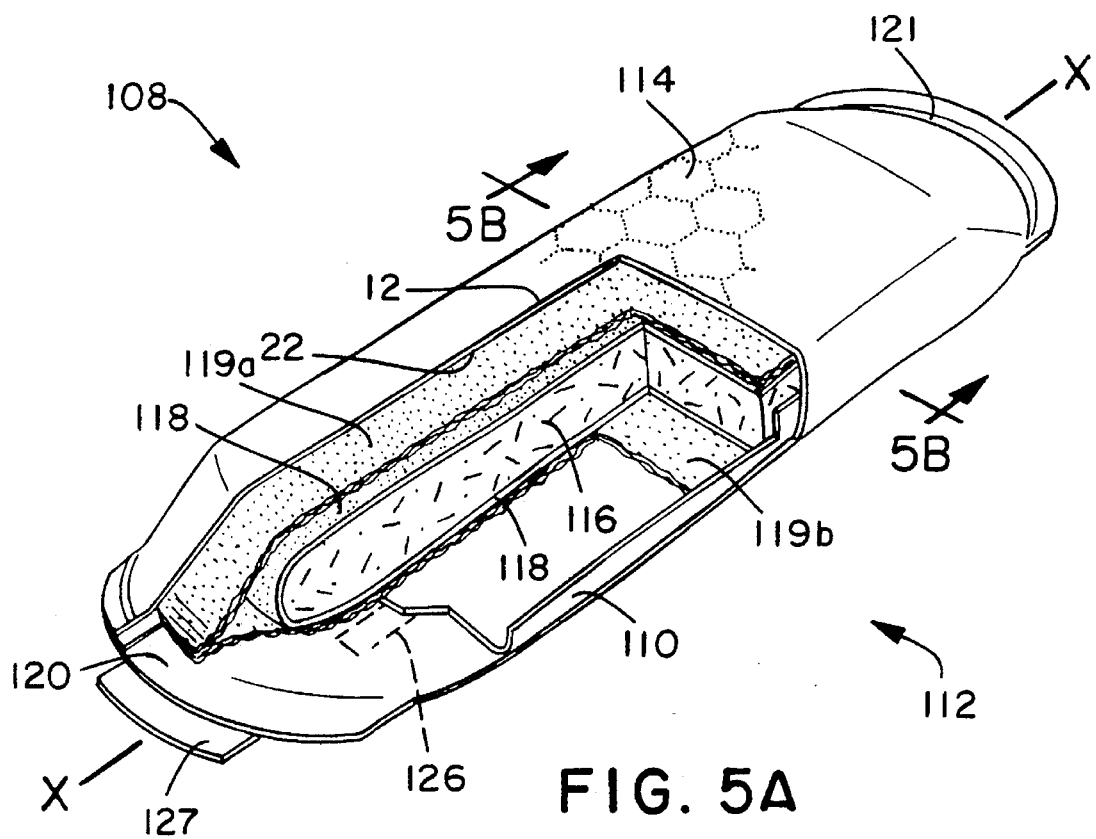
FIG. 5a is a perspective view of another disposable sanitary napkin including the plastic film laminated material of the present invention positioned on the side of the napkin that will be placed next to the wearer's body.
Figure 5B:
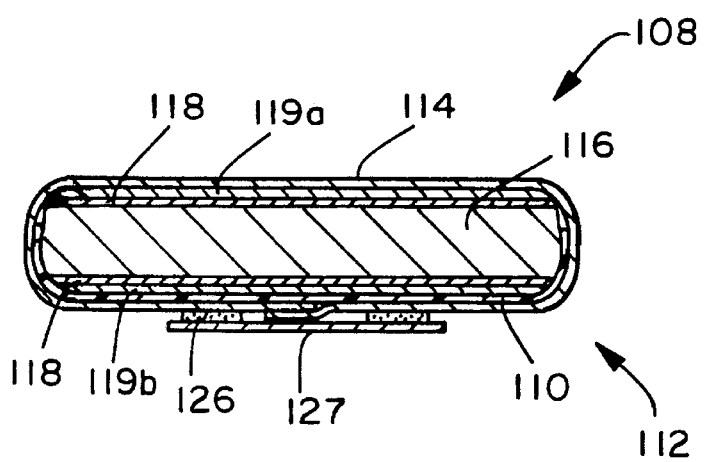

FIGS. 5a and 5b are a perspective view and a cross-sectional view, respectively, of another embodiment of a sanitary napkin 108, similar to that sold under the KOTEX® Maxi trademark by the present assignee, except it includes the film laminated material of the present invention as a cover material. The sanitary napkin 108 has a racetrack profile with essentially parallel, longitudinally-extending sides that are connected by a smooth curve at each end.

The sanitary napkin 108 includes a liquid-impermeable baffle 110, an absorbent structure 112, and a liquid-permeable cover 114 constructed of the film laminated material of the present invention. Film laminated material 114 forms a body facing outer layer 12 comprising a thin thermoplastic film and an inner layer 22 comprising a bonded, substantially unbonded or unbonded carded web formed of a blend of polypropylene and polyester fibers as described above. In this embodiment, film laminated material 114 forms a cover that completely encloses the remaining components of the sanitary napkin 108.

Absorbent structure 112 is aligned along the longitudinal central axis x—x of the sanitary napkin 108. The absorbent structure 112 is a multi-layered configuration constructed of a hydrophilic material 116, a tissue wrap 118 and multiple plies of creped body wadding material 119a and 119b. The hydrophilic material 116 can be made from natural or synthetic fibers, including cellulose fibers, surfactant-treated meltblown fibers, wood pulp fibers, regenerated cellulose or cotton fibers, or coform, which is a blend of pulp and synthetic meltblown fibers. In the embodiment shown, the hydrophilic material 116 is formed of wood pulp fibers. Optionally, the absorbent structure 112 can include a superabsorbent material.

Liquid-impermeable baffle 110 functions to prevent body liquids, absorbed by the absorbent structure 112, from leaking out and soiling or staining an adjacent undergarment. Liquid-impermeable baffle 110 can be made from a micro-embossed polymeric film, such as polyethylene or polypropylene, or it can be made from bicomponent films. In the embodiment shown, baffle 110 is formed of 0.60 mil polypropylene. While baffle 110 can have varying lengths and widths, in the embodiment shown, baffle 110 extends the entire length and width of sanitary napkin 108 and is bonded to cover 114 by known attachment means at each longitudinal end seal 120 and 121.

Sanitary napkin 108 also includes at least one strip of garment adhesive 126 secured to an exterior surface of cover 114. The garment adhesive provides a means for attaching the sanitary napkin 108 to an inside surface of the wearer's undergarment. A releasable peel strip 127 is positioned over the strip of garment adhesive 126 and serves to prevent the adhesive from becoming contaminated before use.

In alternative embodiments (not shown), upper body wadding 119a can be constructed of the film laminated material of this invention. The film laminated material can have varying lengths, ranging from less than, equal to or greater than the length of the hydrophilic material 116. The width of the film laminated material in this configuration can vary from about 1.0 inch (25.4 mm) to about equal to the full width of the sanitary napkin, with about 1.3 inches (34 mm) to about 2.25 inches (57.2) being particularly suitable. In such an embodiment, cover 114 can be constructed of, for example, a spunbonded polypropylene web, either apertured or non-apertured.

While particular configurations of the component parts of sanitary napkins 100 and 108 are shown in FIGS. 4a and 4b, and 5a and 5b, respectively, these components may be assembled into a variety of well-known sanitary napkin configurations. It should be further recognized, however, that in disposable absorbent articles other than sanitary napkins, individual components may be optional, depending upon their intended end uses.

An important property of any bodyside cover or liner material is its softness. In particular, it is important for the liner to be both extremely pliable as well as soft to the touch in consideration of the infant's comfort. The present inventor has observed that the body facing layer 12 of the film laminated material of the present invention exhibits excellent softness characteristics.

Another important property of a bodyside liner material is tensile strength, i.e., the resistance to tearing, and percent elongation prior to tearing. These properties have been measured by the present inventor on a device, such as the Instron Model TM 1000 (Instron Corp. having offices in Canton Mass.), that grips a sample (about 1×6 in. (25.4× 1524 mm)) of a laminated material in a pair of jaws extending the entire width of the sample, and then pulls it apart at a constant rate of extension. The force needed to rupture the material is recorded as the tensile strength and the length of the material before rupture as compared to the original length provides the percent elongation value. These tests can be performed either with the material oriented in the jaws so that the force is applied in the machine direction, MD, or with the material oriented so that the force is applied in the cross direction, CD. It was observed that the film laminated materials made in accordance with the present invention, an example of which is discussed below, exhibited sufficient tensile strength and percent elongation properties.

Yet another property that is particularly important for a liner of an absorbent article, such as a sanitary napkin, is the wettability of the liner. Depending upon the design of the absorbent article, it is usually desirable to have the liner be at least partially wettable in order to facilitate passage of liquid through to the absorbent core. In addition, it is even more desirable to provide a wettability gradient in the liner whereby liquid can be wicked away from the wearer for increased comfort and skin health. In particular, it is desireable to provide, as in the present invention, a body facing layer 12 that is less wettable than the "surge" layer 22, i.e., the layer closest to the absorbent material. In this way, liquid flows more easily through to the absorbent core material than it flows back to the wearer.

Many of the polymers that are suitable to make nonwoven webs are hydrophobic. Specifically, polyolefin fibers are completely hydrophobic. As a result, it is desirable for nonwoven webs made with these polymers to impart a desired level of wettability and hydrophilicity. It is known in the art that wettability of hydrophobic fibers, such as polypropylene, can be increased by the application of water-soluble finishes, typically ranging from about 0.3% to about 0.6%, to the surfaces of such hydrophobic fibers for improving the liquid management properties of such fibers in their end-use applications. In the embodiment described herein, the polypropylene fibers employed can be made wettable by treating the fibers with water-soluble finishes before being formed into nonwoven layer 22.

Another contributing factor in producing the described wettability gradient is the blending of polyester fibers in a desired amount with the polypropylene fibers forming the second nonwoven layer 22. As described above, the differing pore sizes resulting from using the coarser, more resilient polyester fibers in a homogeneous blend of polypropylene and polyester fibers in nonwoven layer 22, produce the required wettability gradient between first layer 12 and second layer 22. Absorbency rate is a measure of the time required for a product to absorb 8 cubic centimeters (cc) of liquid which has been deposited onto a cover material. Therefore, a shorter period of time indicates that the cover material will allow the liquid to pass through more quickly. Blotter rewet values represent a measure of the surface dryness of a material. A lower value indicates a material that exhibits a drier surface. The absorbency rate for the film laminated material of the present invention was tested by subjecting five sample sanitary napkins to an 8 cc insult of synthetic menses, such as Z-Date available from PPG Industries, Inc. having offices in Appleton, Wis. or its equivalent. Each sample was placed on a test block, bodyside up. A Lucite block weighing about 165.5 grams, which provided a unit pressure of about 0.1 psi (7.01 g/cm$^2$), was placed on the sample. The synthetic menses was dispensed into a funnel in the Lucite block and the time required for the sample to absorb all but 2 ml of the synthetic menses was measured. The Lucite block then was removed and the sample was allowed to sit undisturbed for one minute before beginning the blotter rewet test.

The blotter rewet test involved measuring the amount of synthetic menses, in grams, which exited the sample under a uniform application of 1 psi pressure. A pre-weighed piece of blotter paper, such as 100# Riegel available from Sloan Paper Co. having offices in Roswell, Ga. or its equivalent, was placed on the sample. A uniform pressure of 1 psi then was applied to the pad for three minutes. The pressure was removed and the wet blotter paper was weighed to the nearest 0.01 gram. The amount of synthetic menses desorbed from the sample onto the blotter paper was determined by subtracting the dry blotter paper weight from the wet blotter paper weight.

The following Examples are provided only to give a more detailed understanding of the present invention. The particular compositions, proportions, materials and parameters are exemplary and are not intended to specifically limit the scope of the invention.

EXAMPLES

Example 1

A first layer was formed of a thin thermoplastic film (XP-312 manufactured by Edison Plastics having offices in South Plainfield, N.J.), as described above. A second layer was formed of 60% polyester (PET-292 manufactured by Hoechst/AG having offices in Frankfurt, Germany) and 40% polypropylene (PP-71"SOFT-71" manufactured by Danaklon A/S, Inc. having offices in Varde, Denmark) by blending on a conventional carding machine, as described above. The second layer had a basis weight of about 32 g/m$^2$ (0.9 oz/yd$^2$). The first and second layers were thermobonded together by heated bonding rolls as shown in FIGS. 3 and 3a., with the bonding roll contacting the first layer maintained at a temperature of about 176° F. (80° C.) and the bonding roll contacting the second layer maintained at a temperature of about 205° F. (96° C.) The line speed for the bonding rolls was about 50 feet/min. (15 m/min.) and the nip pressure between the bonding rolls was about 295 pli (49 kg/1 cm). The thermobonding process yielded a film laminated material having a spaced apart bonding pattern with apertures formed within the bonding regions and a percent bond area of about 2%.

The resultant film laminated material had the properties set forth in the following table:

TABLE

| Example | Basis Weight (g/m²) | Thickness (in.) | Density (g/cc) | Tensile (g/in.) | | % Elongation | |
|---|---|---|---|---|---|---|---|
| | | | | MD | CD | MD | CD |
| 1 | 44.1 | 0.040 | 0.043 | 474.46 | 200.0 | 59.10 | 15.80 |

Sample sanitary napkins as shown in FIGS. 4a and 4b, including the film laminated material of this Example as the film laminated material 80 of dual component cover 82, had an absorbency rate of about 63.71 seconds and a blotter rewet value of about 2.77 grams.

Example 2

Samples made according to Example 1, except film laminated material 80 was used for the entire dual component cover 82 (i.e., no different second material 81 was used), had an absorbency rate of about 56.53 seconds and a blotter rewet value of about 2.61 grams.

Example 3

Samples made according to Example 1, except film laminated material 80 was used for transfer layer 85 and dual component cover 82 included an apertured thermoplastic film, such as Code No. CKX-215 sold by Applied Extrusion Technologies, Inc. having offices in Middleton, Del. or its functional equivalent, as the film material 81, had an absorbency rate of about 159.18 seconds and a blotter rewet value of about 2.75 grams.

Example 4

Samples made according to Example 1, except transfer layer 85 was removed, had an absorbency rate of about 89.01 seconds and a blotter rewet value of about 2.71 grams.

Example 5

Sample sanitary napkins as shown in FIGS. 5a and 5b, including the film laminated material of Example 1 as the cover 114 and with upper body wadding 119a removed, had an absorbency rate of about 28.78 seconds and a blotter rewet value of about 0.13 gram.

Example 6

Samples made according to Example 5, except a 1.3 inch (34 mm) wide strip of the film laminated material of Example 1 was used as upper body wadding 119a centered on the longitudinal axis of the sample and positioned beneath a spunbonded non-apertured polypropylene cover 114, had an absorbency rate of about 20.34 seconds and a blotter rewet value of about 0.52 gram.

Example 7

Samples made according to Example 6, except a 2.25 in. (57.15 mm) wide strip of the film laminated material of Example 1 was used as upper body wadding 119a centered on the longitudinal axis of the sample, had an absorbency rate of about 17.94 seconds and a blotter rewet value of about 0.30 gram.

It is contemplated that the film laminated material 10 constructed in accordance with the present invention will be tailored and adjusted by those of ordinary skill in the art to accommodate various levels of performance demand imparted during actual use. For example, mild urinary incontinence and menstrual flow pads involve different delivery rates, volumes and timing than infant urine insults. Moreover, the liquid in the surge can vary in terms of the liquid viscosity, surface tension, temperature and other physical properties that could affect the performance of the film laminated material 10 in the various actual product end usages. Accordingly, while this invention has been described by reference to the above embodiments and examples, it will be understood that this invention is capable of further modifications. This application is, therefore, intended to cover any variations, uses or adaptations of the invention following the general principles thereof, and including such departures from the present disclosure as come within known or customary practice in the art to which this invention pertains and fall within the limits of the appended claims.

I claim:

1. An apparatus for forming a film laminated material comprising: means for providing a first film layer comprising a thermoplastic polymeric material;

means for forming a second fibrous layer comprising a plurality of fibers or filaments of one or more thermoplastic polymeric materials;

means for bonding said first and second layers at an interface between said layers in a spaced apart bonding pattern comprising compacted bonding regions having a first degree of bonding separated by second, lesser bonded fiber spans;

said bonding means comprising a first thermal bonding roll and a second thermal bonding roll opposedly positioned relative to each other, each of said bonding rolls having an outer surface in contact with one of said first and second layers as said first and second layers pass therebetween, said first and second bonding rolls having different raised bonding patterns on said outer surfaces thereof, said first bonding roll having a spaced apart raised bonding pattern on the outer surface thereof and said second bonding roll having a plurality of raised bonding points on the outer surface thereof;

means for operating said first bonding roll at a first rotational speed and means for operating said second bonding roll at a second rotational speed, said operating means ensuring that said first and second rotational speeds differ within a range of from about 4% to about 20%;

means for maintaining said first bonding roll at a first bonding temperature within the range of from about 150° F. to about 200° F. and means for maintaining said second bonding roll at a second bonding temperature within the range of from about 190° F. to about 225° F., said maintaining means maintaining said first and second bonding rolls at different bonding temperatures; and said bonding rolls forming apertures within said bonding regions, said apertures being substantially free of fibers through the thickness of each said layer.

2. An apparatus for forming a film laminated material according to claim 1 further comprising first bonding means for bonding fibers of said second fibrous layer to one another.

3. An apparatus for forming a film laminated material according to claim 1 wherein the formation of said apertures is substantially limited to said bonding regions.

4. An apparatus for forming a film laminated material according to claim 1 wherein said bonding means bonds said first and second layers together in a spaced apart bonding pattern such that the resulting film laminated material has a percent bond area of from about 1% to about 6%.

5. An apparatus for forming a film laminated material according to claim 1 wherein said spaced apart bonding pattern is formed by points of contact between said raised bonding patterns on said outer surfaces of said first and second bonding rolls.

6. An apparatus for forming a film laminated material according to claim 5 wherein said apertures are formed by points of contact between said raised bonding patterns on said outer surfaces of said first and second bonding rolls.

7. An apparatus for forming a film laminated material according to claim 1 wherein said first bonding roll has a percent bond area of from about 9% to about 20% and said second bonding roll has a percent bond area of from about 10% to about 30%.

8. An apparatus for forming a film laminated material according to claim 1 wherein said raised bonding patterns of said first and second bonding rolls are configured to optimize the number of said apertures formed within said bonding regions.

9. An apparatus for forming a film laminated material according to claim 1 wherein said first film layer contacts said first bonding roll and said second fibrous layer contacts said second bonding roll during rotation and heating of said rolls.

10. An apparatus for forming a film laminated material according to claim 1 wherein said operating means rotate said first and second bonding rolls such that said first film layer and said second fibrous layer passing therebetween have a line speed ranging from about 12 meters per minute to about 100 meters per minute.

11. An apparatus for forming a film laminated material according to claim 1 further comprising means for producing a nip pressure of from about 60 pounds per linear inch to about 400 pounds per linear inch within a nip formed between said first and second bonding rolls.

* * * * *